United States Patent
Wang et al.

(10) Patent No.: US 11,473,119 B2
(45) Date of Patent: Oct. 18, 2022

(54) METHOD FOR DETERMINING OPTIMUM PRESERVATION TEMPERATURE OF SULFUR AUTOTROPHIC DENITRIFYING BACTERIA BIOFILM

(71) Applicant: Jiangnan University, Wuxi (CN)

(72) Inventors: Shuo Wang, Wuxi (CN); Xiaodong Wang, Wuxi (CN); Hui Lv, Wuxi (CN); Ji Li, Wuxi (CN); Yan Wang, Wuxi (CN)

(73) Assignee: Jiangnan University, Wuxi (CN)

( * ) Notice: Subject to any disclaimer, the term of this patent is extended or adjusted under 35 U.S.C. 154(b) by 469 days.

(21) Appl. No.: 16/656,391

(22) Filed: Oct. 17, 2019

(65) Prior Publication Data
US 2020/0048677 A1 Feb. 13, 2020

(30) Foreign Application Priority Data
Oct. 29, 2018 (CN) .......................... 201811273455.5

(51) Int. Cl.
*C12Q 1/02* (2006.01)
*G01N 15/14* (2006.01)
*G01N 15/10* (2006.01)

(52) U.S. Cl.
CPC ............... *C12Q 1/02* (2013.01); *G01N 15/14* (2013.01); *G01N 2015/1006* (2013.01)

(58) Field of Classification Search
None
See application file for complete search history.

(56) References Cited

PUBLICATIONS

Oh et al. "Kinetics and physiological characteristics of autotrophic dentrification by denitrifying sulfur bacteria" Water Science and Technology vol. 42 Nos. 3-4 pp. 59-68 (Year: 2000).*

* cited by examiner

*Primary Examiner* — Thane Underdahl
(74) *Attorney, Agent, or Firm* — IPRO, PLLC; Na Xu

(57) ABSTRACT

The present disclosure discloses to a method for determining optimum preservation temperature of a sulfur autotrophic denitrifying bacteria biofilm, and belongs to the technical field of environment engineering. The method of the present disclosure comprises: determining the cell activity state of a sulfur autotrophic denitrifying bacteria biofilm preserved at different temperatures by flow cytometry, and determining the preservation temperature of the cell activity state closest to the cell activity state of the sulfur autotrophic denitrifying bacteria in pilot operation as the optimum preservation temperature. The cell activity state and performance effect are verified to be reliable after activity recovery by the test data. The method of the present disclosure can simplify the microbial activity recovery process of the sulfur autotrophic denitrifying bacteria biofilm, quickly start the sulfur autotrophic denitrifying bacteria biofilm sewage treatment, enable the removal rate of nitrate nitrogen and total nitrogen in a sewage treatment plant to reach 96% and 88% or above respectively, achieve the effects of energy saving and consumption reduction at the same time, and have very high industrial feasibility.

13 Claims, 1 Drawing Sheet

METHOD FOR DETERMINING OPTIMUM PRESERVATION TEMPERATURE OF SULFUR AUTOTROPHIC DENITRIFYING BACTERIA BIOFILM

TECHNICAL FIELD

The disclosure herein relates to the field of a method for determining optimum preservation temperature of a sulfur autotrophic denitrifying bacteria biofilm, and belongs to the technical field of environment engineering.

BACKGROUND

Total nitrogen up-to-standard discharge in sewage treatment plants has always been a difficult point in operation of the sewage treatment plants. As sewage treatment discharge standards increase gradually, a large amount of carbon sources are added to an anoxic pond or a denitrification filter for enhancing denitrification. However, the method of adding carbon sources is not only a waste of petroleum resources (the added carbon sources such as acetic acid or sodium acetate, are generally products of petroleum refining), but also significantly increases the operating cost of sewage treatment, in turn generating resistance to the energy-saving and consumption-reducing operation of the sewage treatment plant. Therefore, sewage denitrification technologies based on land-saving targets and zero additional carbon sources have received increasing attention. Sulfur autotrophic denitrification refers to the process of converting nitrate nitrogen with a relatively high concentration in a secondary sedimentation tank of a sewage treatment plant into nitrogen under the anoxic conditions, with autotrophic denitrifying bacteria using elemental sulfur as an electron donor. The process does not require additional carbon sources, and only needs to replace the carbon sources added in a denitrification filter of a deep treatment unit with elemental sulfur particles, and the autotrophic denitrifying bacteria adhere to the elemental sulfur particles. Through autotrophic denitrification, ultra-low discharge of total nitrogen in sewage treatment plants and stable operation of energy saving and consumption reduction are realized. The chemical reaction equation is as follows:

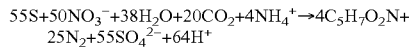

$$55S + 50NO_3^- + 38H_2O + 20CO_2 + 4NH_4^+ \rightarrow 4C_5H_7O_2N + 25N_2 + 55SO_4^{2-} + 64H^+$$

The autotrophic denitrifying bacteria have a low growth rate and a long generation time, and will adhere to the elemental sulfur particles to form a biofilm to enhance the removal of nitrate nitrogen. If the cultured mature sulfur autotrophic denitrifying bacteria biofilm with good total nitrogen removal effect is preserved and applied to a sewage treatment plant with difficulty in up-to-standard total nitrogen and limited operation expenses, the time for the total nitrogen up-to-standard discharge of the sewage treatment plant can be effectively shortened, carbon source materials resources are saved, and the operation cost of the sewage treatment plant is reduced. Temperature is an important parameter affecting the microbial activity. Determining the temperature most suitable for the preservation of the sulfur autotrophic denitrifying bacteria biofilm helps to simplify the microbial activity recovery process of the sulfur autotrophic denitrifying bacteria biofilm, shorten the start-up time of engineering application of the sulfur autotrophic denitrifying bacteria biofilm, and achieve energy saving and consumption reduction effects. At present, there has been no research on the activity recovery of sulfur autotrophic denitrifying bacteria biofilm, which has affected the engineering application of the sulfur autotrophic denitrifying bacteria biofilm.

SUMMARY

In order to simplify the recovery process of the microbial activity of a sulfur autotrophic denitrifying bacteria biofilm, enable the total nitrogen of a sewage treatment plant to be discharged up to standard within a short time, and at the same time achieve the effects of energy saving and consumption reduction, the present disclosure characterize the cell activity state of the sulfur autotrophic denitrifying bacteria biofilm preserved under different temperature conditions based on flow cytometry. The characterization results of flow cytometry are verified by the activity recovery effect of the sulfur autotrophic denitrifying bacteria biofilm and the cell activity state after the recovery of microbial activity. Finally, a method for determining the optimum preservation temperature of the sulfur autotrophic denitrifying bacteria biofilm based on flow cytometry is established to provide technical support for ultra-low discharge of total nitrogen and energy-saving and consumption-reducing operation of sewage treatment plants.

A first objective of the present disclosure is to provide a method for determining an optimum preservation temperature of a sulfur autotrophic denitrifying bacteria biofilm. The method includes: determining the cell activity state of a sulfur autotrophic denitrifying bacteria biofilm preserved at different temperatures by flow cytometry, and determining the preservation temperature of the cell activity state closest to the cell activity state of the sulfur autotrophic denitrifying bacteria biofilm in pilot operation as the optimum preservation temperature; and determination of the cell activity state of the sulfur autotrophic denitrifying bacteria biofilm includes determination of the contents of living cells, early apoptotic cells, late apoptotic cells and dead cells.

In an embodiment of the present disclosure, the method for determining the optimum temperature by flow cytometry includes:

(1) preparation of a test sample solution of the sulfur autotrophic denitrifying bacteria biofilm: diluting a sample of the sulfur autotrophic denitrifying bacteria biofilm with a buffer, uniformly mixing and passing through a hydrotalcite-containing filter device; centrifuging the filtered sample, and retaining the supernatant; blow washing the cells with a pre-cooled buffer, centrifuging and washing twice; taking the supernatant as a sample and uniformly mixing with an appropriate amount of 10× Annexin V Binding Buffer; and (2) determining the cell activity state of each sample solution by flow cytometry.

In an embodiment of the present disclosure, the buffer includes a phosphate buffer.

In an embodiment of the present disclosure, the buffer includes 39% v/v sodium dihydrogen phosphate (0.2 mol/L) and 61.0% v/v disodium hydrogen phosphate (0.2 mol/L).

In an embodiment of the present disclosure, the optimum pH of a pilot operation system is 6.2-7.0.

In an embodiment of the present disclosure, the pH of the buffer is 6.2-6.8, and the dilution volume ratio of the buffer to the sulfur autotrophic denitrifying bacteria biofilm is (8-10):1.

In an embodiment of the present disclosure, the preparation of the test sample solution of the sulfur autotrophic denitrifying bacteria biofilm may also include: filtering the effluent treated by a sulfur autotrophic denitrification process through a hydrotalcite layer to obtain a filtrate; diluting the sulfur autotrophic denitrifying bacteria biofilm with the filtrate in a dilution volume ratio of (8-10):1, centrifuging and taking supernatant; diluting the supernatant with the buffer, centrifuging and retaining the supernatant; then blow washing the cells with a pre-cooled buffer, centrifuging and washing twice; then taking the supernatant as a sample and uniformly mixing with an appropriate amount of 10× Annexin V Binding Buffer.

In an embodiment of the present disclosure, the sulfur autotrophic denitrification process can refer to CN201611004494.6. The effluent treated by the sulfur autotrophic denitrification process has a COD concentration of 40-50 mg/L, an ammonia nitrogen $NH_4^+$—N concentration of 0.5-1.0 mg/L, a nitrate nitrogen $NO_3^-$—N concentration of 1-4 mg/L, and a sulfate concentration of 160-240 mg/L.

In an embodiment of the present disclosure, the hydrotalcite in the method can remove sulfate from the mixed liquid.

In an embodiment of the present disclosure, the filter device further includes a nylon membrane with a pore size of 15-25 μm.

In an embodiment of the present disclosure, the packing height of the hydrotalcite filter layer in the filter device is 2 m.

In an embodiment of the present disclosure, a preparation method of the hydrotalcite includes: weighing $Mg(NO_3)_2 \cdot 6H_2O$ and $Al(NO_3)_3 \cdot 9H_2O$ according to a molar ratio of magnesium to aluminum of 3:1, and mixing and dissolving in 1 L of redistilled water to obtain a mixed salt solution; further, weighing a certain amount of NaOH and $Na_2CO_3$ and dissolving in redistilled water to obtain a mixed alkali solution, wherein $n(CO_3^{2-})/n(Al^{3+})$ and $n(NaOH)/n(Mg^{2+}+Al^{3+})$ are both 2.0; quickly mixing the salt solution and the alkali solution, stirring, adjusting the pH of the solution to 9.5 to obtain a white slurry suspension, and placing the white slurry suspension in a constant temperature water bath at 75° C., reacting for 12 h; and after a sample is cooled, performing suction filtration on the sample and washing an obtained solid to neutrality, drying at 80° C., and finely grinding to obtain the hydrotalcite.

In an embodiment of the present disclosure, the centrifugal speed is 5000-10000 rpm.

In an embodiment of the present disclosure, the mixed volume ratio of the sample supernatant to the 10× Annexin V Binding Buffer is 1:(2-4).

In an embodiment of the present disclosure, determination of the cell activity state of each sample solution by flow cytometry includes: adding 0.5 μl of PI stain to a control FITC Annexin V group, adding 0.5 μl of FITC Annexin V to a control PI group, adding 0.5 μl of FITC Annexin V and 0.5 μl of PI to a test group, after uniformly mixing, performing incubation at room temperature in the dark, and then detecting by flow cytometry.

In an embodiment of the present disclosure, the incubation time is 10-20 min.

A second objective of the present disclosure is to provide a method for rapidly starting a sulfur autotrophic denitrifying bacteria biofilm project. The method includes: determining an optimum preservation temperature by the above method, placing a cultured mature sulfur autotrophic denitrifying bacteria biofilm in a preservation medium for preservation at the optimum preservation temperature, and after the activity is recovered, starting the sulfur autotrophic denitrifying bacteria biofilm project.

In an embodiment of the present disclosure, the COD concentration of the preservation medium is 40-50 mg/L, the concentration of $NH_4^+$—N is 0.3-0.5 mg/L, and the concentration of $NO_3^-$—N is 8-12 mg/L.

In an embodiment of the present disclosure, activity recovery is inoculation of the sulfur autotrophic denitrifying bacteria biofilm into a bioreactor, wherein the bioreactor has an effective volume of 20.0-40.0 L and an effective height of 120-180 cm, coarse sand and stones are laid at the bottom to support the upper elemental sulfur particles, the upper part of the coarse sand and the stones is the elemental sulfur particles, and the porosity is about 35-45%.

A third objective of the present disclosure is to provide a method of sewage treatment, using the above method to rapidly start a sulfur autotrophic denitrifying bacteria biofilm project.

The present disclosure characterizes the proportions of living cells, early apoptotic cells, late apoptotic cells and dead cells in the sulfur autotrophic denitrifying bacteria biofilm by flow cytometry, carries out correlation analysis with the characteristic indexes of the sulfur autotrophic denitrifying bacteria biofilm activity recovery process, and establishes a method for determining the optimum preservation temperature of the sulfur autotrophic denitrifying bacteria biofilm based on flow cytometry. Use of the method can omit the step of recovering the activity of the sulfur autotrophic denitrifying bacteria biofilm, effectively help the sewage treatment plant that prepare to use the sulfur autotrophic denitrifying bacteria biofilm technology to carry out up-to-standard discharge of nitrate nitrogen and total nitrogen to achieve energy saving and consumption reduction operation, reduce the operation cost, effectively shorten the startup time of sulfur autotrophic denitrifying bacteria biofilm engineering application, maintain long-term stable operation of the sulfur autotrophic denitrifying bacteria biofilm process, and have high feasibility.

DETAILED DESCRIPTION

Figure 1:
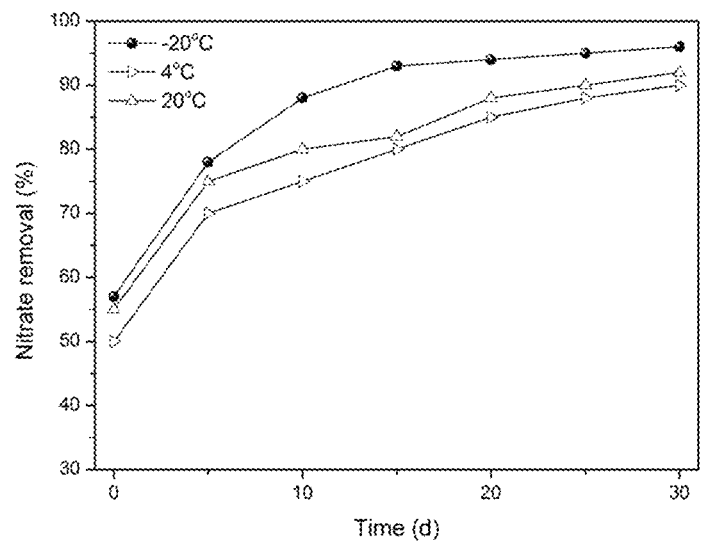
FIG. 1 shows the nitrate nitrogen removal rate of preserved sulfur autotrophic denitrifying bacteria biofilm.

In order to more clearly understand the technical content of the present disclosure, the following examples are specifically described, and the purpose is to better understand the present disclosure rather than limiting the scope of the present disclosure.

Example 1

Preservation culture of sulfur autotrophic denitrifying bacteria biofilm:

The preservation temperature of the sulfur autotrophic denitrifying bacteria biofilm was set to −20° C., 4° C. and 20° C. About 90 sulfur autotrophic denitrifying bacteria biofilms in a pilot reaction device were taken out and averaged into three equal parts to be respectively placed in a 500 ml serum bottle containing 250 ml of a preservation medium (the serum bottle was prefilled with $N_2$ to discharge $O_2$ in the air). The preservation medium is the effluent from a secondary sedimentation tank of a sewage treatment plant, and has a COD concentration of 40-50 mg/L, an $NH_4^+$—N concentration of 0.3-0.5 mg/L, and an $NO_3^-$—N concentration of 8-12 mg/L. The serum bottles (3 parallel samples at each preservation temperature) were placed at −20° C., 4° C. and 20° C. respectively, and preserved in static shading.

During the commissioning operation of a pilot system, the pH of the effluent fluctuated between 6.2 and 7.0. After stable operation, the pH of the effluent was generally at 6.4-6.8.

Cell state test of preserved sulfur autotrophic denitrifying bacteria biofilm:

(1) 100 ml of sulfur autotrophic denitrifying bacteria biofilm mixed liquid was taken, diluted to 1 L with a phosphate buffer of pH 6.6, and stirred on a magnetic stirrer for 5 min to break the biofilm into flocs and ensure uniform distribution;

(2) after the sample passed through a hydrotalcite filter layer to remove the sulfate in a liquid phase, the floc sample was filtered through a nylon membrane with the pore size of 20 μm and centrifuged at 8000 rpm for 5 min;

(3) the precipitate was placed in a 50 ml centrifuge tube and the sample was centrifuged at 8000 rpm for 5 min;

(4) the centrifuged sample supernatant was pipetted with a pipette, about 0.1 ml of sample was left, and the cells were blow washed with a pre-cooled phosphate buffer (pH 7.8), centrifuged and washed twice;

(5) the supernatant of the centrifuged sample was pipetted, and about 0.1 ml of sample was left and mixed with 0.3 ml of 10× Annexin V Binding Buffer; and (6) 0.5 μl of PI stain was added to a control FITC Annexin V group, 0.5 μl of FITC Annexin V was added to a control PI group, 0.5 μl of FITC Annexin V and 0.5 μl of PI were added to a test group, after uniformly mixing, incubation was performed at room temperature in the dark for 15 min, and then detection was performed by flow cytometry.

The selection of filter pore size when preparing samples is especially important. If the pore size is too large, more biological flocs will be introduced, resulting in uneven staining and affecting the final result. If the pore size is too small, biological flocs cannot be effectively obtained.

The cell state test results of the sulfur autotrophic denitrifying bacteria biofilm are shown in Table 1. The proportion of living cells of the sulfur autotrophic denitrifying bacteria biofilm in a biochemical reaction tank of the sewage treatment plant is high, indicating that the sewage treatment plant has a good operation effect. The sulfur autotrophic denitrifying bacteria biofilm preserved at −20° C., 4° C. and 20° C. was used for determining the cell state of the sulfur autotrophic denitrifying bacteria biofilm after being preserved for more than 100 d, the results are shown in Table 1. The proportion of living cells of the sulfur autotrophic denitrifying bacteria biofilm in the pilot reaction device was high, indicating that the sulfuric autotrophic denitrification effect of the pilot system was good. The content of living cells used for determining the sulfur autotrophic denitrifying bacteria biofilm preserved at 20° C. was the lowest, indicating that 20° C. was not suitable for preserving the sulfur autotrophic denitrifying bacteria biofilm. The proportion of living cells of the sulfur autotrophic denitrifying bacteria biofilm preserved at 4° C. was 47.1%, and the proportion of late apoptotic cells and dead cells was about 48.3%. The relatively high proportion of late apoptotic cells and dead cells indicates that 4° C. is also not suitable for preserving the sulfur autotrophic denitrifying bacteria biofilm. When the preservation temperature was −20° C., the proportion of living cells of the sulfur autotrophic denitrifying bacteria biofilm reached 60.8%, which was only 23.4% lower than the proportion of living cells of the sulfur autotrophic denitrifying bacteria biofilm in the pilot reaction device, and meanwhile, the proportion of dead cells was about 20.4%, which is close to the proportion of dead cells of the sulfur autotrophic denitrifying bacteria biofilm in the pilot reaction device. Therefore, it was preliminarily determined that −20° C. was the optimum temperature for preserving the sulfur autotrophic denitrifying bacteria biofilm.

TABLE 1

Cell activity state of preserved sulfur autotrophic denitrifying bacteria biofilm (%)

| Sulfur autotrophic denitrifying bacteria biofilm | Living cells | Early apoptotic cells | Late apoptotic cells | Dead cells |
|---|---|---|---|---|
| Pilot operation system | 79.4 ± 3.8 | 0.1 ± 0.1 | 0.1 ± 0.1 | 20.5 ± 1.5 |
| Preserved at −20° C. | 60.8 ± 3.2 | 3.0 ± 0.2 | 15.8 ± 1.0 | 20.4 ± 1.7 |
| Preserved at 4° C. | 47.1 ± 3.0 | 4.6 ± 0.9 | 23.7 ± 1.8 | 24.6 ± 2.2 |
| Preserved at 20° C. | 36.3 ± 3.0 | 9.2 ± 1.2 | 30.4 ± 2.7 | 24.1 ± 0.8 |

Example 2 Conditions for Activity Recovery of Preserved Sulfur Autotrophic Denitrifying Bacteria Biofilm Sulfur autotrophic denitrifying bacteria biofilms from different serum bottles were inoculated into bioreactors (with an effective volume of 20.0 L and an effective height of 150 cm) for carrying out activity recovery on the sulfur autotrophic denitrifying bacteria biofilms. The sulfur autotrophic denitrifying bacteria biofilms preserved at −20° C., 4° C. and 20° C. were placed in R1, R2 and R3 respectively. Coarse sand and stones were laid at 20 cm of the bottom of the bioreactor to support the upper elemental sulfur particles, the upper part of the coarse sand and the stones were 100 cm of elemental sulfur particles, and the porosity was about 40%.

Example 3 Characteristics of Sulfur Autotrophic Denitrifying Bacteria Biofilm after Activity Recovery After 30 days of activity recovery, the characteristics of the sulfur autotrophic denitrifying bacteria biofilms in R1, R2 and R3 are shown in Table 2. After activity recovery of the sulfur autotrophic denitrifying bacteria biofilm, the nitrate nitrogen removal rate of the sulfur autotrophic denitrifying bacteria biofilm preserved at 4° C. and 20° C. is lower than that of the sulfur autotrophic denitrifying bacteria biofilm before preservation, and only the nitrate nitrogen removal rate of the sulfur autotrophic denitrifying bacteria biofilm preserved at −20° C. is the same as that before preservation. The total nitrogen removal rate of the sulfur autotrophic denitrifying bacteria biofilm at different preservation temperatures is all lower than that before preservation. After activity recovery, the total nitrogen removal rate of the sulfur autotrophic denitrifying bacteria biofilm preserved at 20° C. and −20° C. is relatively close to that of the sulfur autotrophic denitrifying bacteria biofilm before preservation, but the total nitrogen removal rate of the sulfur autotrophic denitrifying bacteria biofilm preserved at 4° C. is relatively low.

Generally, the nitrate nitrogen removal rate and total nitrogen removal rate of the sulfur autotrophic denitrifying bacteria biofilm are 140 $gNO_3^- - N/(m^3 \cdot h)$ and 125 $gTN/(m^3 \cdot h)$, respectively. The time of the sulfur autotrophic denitrifying bacteria biofilm acclimated in the pilot operation system reaching the same nitrate nitrogen removal rate and total nitrogen removal rate are 65 d and 70 d, respectively. After activity recovery of the preserved sulfur autotrophic denitrifying bacteria biofilm, the time of the sulfur autotrophic denitrifying bacteria biofilm in R1 reaching the same nitrate nitrogen removal rate and total nitrogen removal rate were 12 d and 15 d, respectively, the time of the sulfur autotrophic denitrifying bacteria biofilm in R2 reaching the same nitrate nitrogen removal rate and total nitrogen removal rate were 21 d and 22 d, respectively, and the time of the sulfur autotrophic denitrifying bacteria biofilm in R3 reaching the same nitrate nitrogen removal rate and total nitrogen removal rate were 18 d and 20 d, respectively. It is indicated that the sulfur autotrophic denitrifying bacteria biofilms after activity recovery all have good denitrification effect, wherein the sulfur autotrophic denitrifying bacteria biofilm preserved at −20° C. has the shortest recovery time of microbial activity and −20° C. is suitable for preserving the sulfur autotrophic denitrifying bacteria biofilm.

TABLE 2

Characteristics of sulfur autotrophic denitrifying bacteria biofilm after preservation and activity recovery

| | Nitrate nitrogen removal rate $gNO_3^-$-$N/(m^3 \cdot h)$ | Total nitrogen removal rate $gTN/(m^3 \cdot h)$ | Required time (d) when nitrate nitrogen removal rate is greater than 140 $gNO_3^-$-$N/(m^3 \cdot h)$ | Required time (d) when total nitrogen removal rate exceeds 125 $gTN/(m^3 \cdot h)$ |
|---|---|---|---|---|
| Pilot operation system | 164.1 | 145.0 | 65 | 70 |
| After preservation of sulfur autotrophic denitrifying bacteria biofilm | | | | |
| After preservation at −20° C. | 103.5 | 90.9 | — | — |
| After preservation 4° C. | 75.5 | 66.4 | — | — |
| After preservation 20° C. | 93.9 | 65.9 | — | — |
| After activity recovery of sulfur autotrophic denitrifying bacteria biofilm | | | | |
| Sulfur autotrophic denitrifying bacteria biofilm preserved at −20° C. | 165.0 | 137.5 | 12 | 15 |
| Sulfur autotrophic denitrifying bacteria biofilm preserved at 4° C. | 144.5 | 125.1 | 21 | 22 |
| Sulfur autotrophic denitrifying bacteria biofilm preserved at 20° C. | 147.1 | 136.8 | 18 | 20 |

Figure 2:
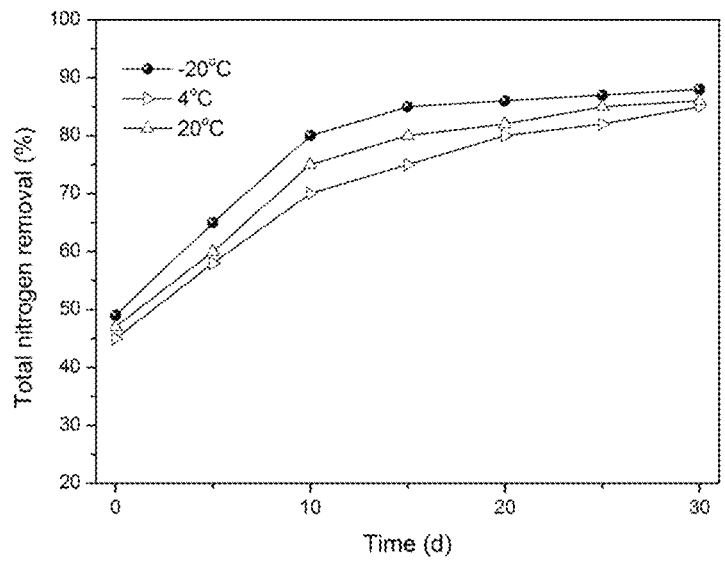
FIG. 2 shows the total nitrogen removal rate of preserved sulfur autotrophic denitrifying bacteria biofilm.

Example 4 Removal Efficiency of Sulfur Autotrophic Denitrifying Bacteria Biofilm to Pollutants after Activity Recovery After the activity recovery process, the nitrate nitrogen and total nitrogen removal rate of the sulfur autotrophic denitrifying bacteria biofilm at different preservation temperatures gradually increased (FIG. 1 and FIG. 2), and the nitrate nitrogen removal rate and total nitrogen removal rate exceed 96% and 88%, respectively. On the 15th day of activity recovery, the sulfur autotrophic denitrifying bacteria biofilm in R1 had the best removal effect on the nitrate nitrogen and total nitrogen, and the nitrate nitrogen and total nitrogen removal rate increased steadily. This result also corresponds to the fastest recovery of higher nitrate nitrogen removal rate and total nitrogen removal rate of the sulfur autotrophic denitrifying bacteria biofilm in R1 in Table 2. It is indicated that the condition of −20° C. is more suitable for preserving the sulfur autotrophic denitrifying bacteria biofilm, and has high feasibility in practical application.

Example 5 Correlation Between Sulfur Autotrophic Denitrifying Bacteria Biofilm Characteristics and Sludge Cell State after Activity Recovery After 30 days of activity recovery of the sulfur autotrophic denitrifying bacteria biofilm, the cell state of the sulfur autotrophic denitrifying bacteria biofilm was analyzed by flow cytometry, the results are shown in Table 3. The content of living cells in the sulfur autotrophic denitrifying bacteria biofilm at different preservation temperatures is basically the same as that in the sulfur autotrophic denitrifying bacteria biofilm in the pilot operation system, indicating that after activity recovery, the sulfur autotrophic denitrifying bacteria biofilm can achieve stable nitrate nitrogen and total nitrogen removal effects. Where, the proportion of living cells in the sulfur autotrophic denitrifying bacteria biofilm in R1 was the highest (79.5%±4.0%), and the proportion of late apoptotic cells (5.6%±1.0%) and dead cells (11.1%±1.1%) were the lowest, indicating that the sulfur autotrophic denitrifying bacteria biofilm has the highest activity under the preservation condition of −20° C., and the condition of −20° C. is suitable for preserving the sulfur autotrophic denitrifying bacteria biofilm.

TABLE 3

Cell activity state of sulfur autotrophic denitrifying bacteria biofilm after activity recovery (%)

| Sulfur autotrophic denitrifying bacteria biofilm | Living cells | Early apoptotic cells | Late apoptotic cells | Dead cells |
|---|---|---|---|---|
| Pilot operation system | 82.5 ± 4.1 | 2.5 ± 0.5 | 4.3 ± 0.8 | 10.7 ± 1.0 |
| Preserved at −20° C. | 79.5 ± 4.0 | 3.8 ± 0.5 | 5.6 ± 1.0 | 11.1 ± 1.1 |
| Preserved at 4° C. | 75.0 ± 4.2 | 4.9 ± 0.5 | 7.2 ± 0.8 | 12.9 ± 1.2 |
| Preserved at 20° C. | 77.8 ± 4.0 | 5.0 ± 0.7 | 6.0 ± 0.8 | 11.2 ± 1.2 |

According to Correl correlation analysis, as shown in Table 4, there is a high correlation between the nitrate nitrogen removal rate and total nitrogen removal rate of the sulfur autotrophic denitrifying bacteria biofilm and the proportion of living cells of the sulfur autotrophic denitrifying bacteria biofilm, and the correlation coefficients are respectively 0.9577 and 0.9450, indicating that use of the proportion of living cells of the sulfur autotrophic denitrifying bacteria biofilm as a method for evaluating the activity of the sulfur autotrophic denitrifying bacteria biofilm has high feasibility. Meanwhile, in the preserved sulfur autotrophic denitrifying bacteria biofilm, the proportion of living cells of the sulfur autotrophic denitrifying bacteria biofilm at the preservation condition of −20° C. is the highest, which is consistent with the results of the proportion of living cells of the sulfur autotrophic denitrifying bacteria biofilm in R1 after activity recovery.

TABLE 4

Correlation between sulfur autotrophic denitrifying bacteria biofilm characteristics and cell activity state after activity recovery

|  | Sulfur autotrophic denitrifying bacteria biofilm preserved at −20° C. | Sulfur autotrophic denitrifying bacteria biofilm preserved at 4° C. | Sulfur autotrophic denitrifying bacteria biofilm preserved at 20° C. |
| --- | --- | --- | --- |
| Nitrate nitrogen removal rate $gNO_3^-$-N/($m^3 \cdot h$) | 165.0 | 144.5 | 147.1 |
| Total nitrogen removal rate $gTN/(m^3 \cdot h)$ | 137.5 | 125.1 | 136.8 |
| Proportion of living cells (%) | 79.5 ± 4.0 | 75.0 ± 4.2 | 76.8 ± 4.0 |
| Correlation between nitrate nitrogen removal rate and proportion of living cells |  | 0.9577 |  |
| Correlation between total nitrogen removal rate and proportion of living cells |  | 0.9450 |  |

Therefore, it is determined that −20° C. is the optimum temperature for preserving the sulfur autotrophic denitrifying bacteria biofilm. Flow cytometry can be used as a basis for determining the optimum preservation temperature of the sulfur autotrophic denitrifying bacteria biofilm. Flow cytometry is easy to operate and fast and easy to obtain accurate and reliable data, can omit the activity recovery process of the sulfur autotrophic denitrifying bacteria biofilm, and is of great significance for the preservation and activity recovery of the sulfur autotrophic denitrifying bacteria biofilm.

Comparative Example 1

Preservation culture of sulfur autotrophic denitrifying bacteria biofilm:

The preservation temperature of the sulfur autotrophic denitrifying bacteria biofilm was set to −20° C., 4° C. and 20° C. About 90 sulfur autotrophic denitrifying bacteria biofilms in the pilot reaction device were taken out and averaged into three equal parts to be respectively placed in a 500 ml serum bottle containing 250 ml of the preservation medium (the serum bottle was prefilled with $N_2$ to discharge $O_2$ in the air). The preservation medium is the effluent from a secondary sedimentation tank of a sewage treatment plant, and has a COD concentration of 40-50 mg/L, an $NH_4^+$—N concentration of 0.3-0.5 mg/L, and an $NO_3^-$—N concentration of 8-12 mg/L. The serum bottles (3 parallel samples at each preservation temperature) were placed at −20° C., 4° C. and 20° C. respectively, and preserved in static shading.

Cell state test of preserved sulfur autotrophic denitrifying bacteria biofilm:

(1) 100 ml of sulfur autotrophic denitrifying bacteria biofilm mixed liquid was taken, diluted to 1 L with a phosphate buffer of pH 6.6, and stirred on a magnetic stirrer for 5 min to break the biofilm into flocs and ensure uniform distribution;

(2) the floc sample was filtered through a nylon membrane with the pore size of 20 μm and centrifuged at 8000 rpm for 5 min;

(3) the precipitate was placed in a 50 ml centrifuge tube and the sample was centrifuged at 8000 rpm for 5 min;

(4) the centrifuged sample supernatant was pipetted with a pipette, about 0.1 ml of sample was left, and the cells were blow washed with a pre-cooled phosphate buffer (pH 7.8), centrifuged and washed twice;

(5) the supernatant of the centrifuged sample was pipetted, and about 0.1 ml of sample was left and mixed with 0.3 ml of 10× Annexin V Binding Buffer; and (6) 0.5 μl of PI stain was added to a control FITC Annexin V group, 0.5 μl of FITC Annexin V was added to a control PI group, 0.5 μl of FITC Annexin V and 0.5 μl of PI were added to a test group, after uniformly mixing, incubation was performed at room temperature in the dark for 15 min, and then detection was performed by flow cytometry.

The cell state test results of the sulfur autotrophic denitrifying bacteria biofilm are shown in Table 5.

TABLE 5

Cell activity state of preserved sulfur autotrophic denitrifying bacteria biofilm (without being adsorbed by hydrotalcite layer)

| Sulfur autotrophic denitrifying bacteria biofilm | Living cells | Early apoptotic cells | Late apoptotic cells | Dead cells |
| --- | --- | --- | --- | --- |
| Pilot operation system | 51.5% ± 4.9% | 15.8% ± 1.9% | 15.7% ± 1.8% | 17.0% ± 1.9% |
| Preserved at −20° C. | 58.8% ± 5.1% | 13.5% ± 2.1% | 13.7% ± 2.0% | 14.0% ± 2.1% |
| Preserved at 4° C. | 45.7% ± 4.7% | 18.0% ± 2.7% | 18.5% ± 2.5% | 17.8% ± 2.4% |
| Preserved at 20° C. | 43.3% ± 4.7% | 19.0% ± 3.0% | 19.2% ± 3.5% | 18.5% ± 2.9% |

From the results of Table 5, it is found that the samples that have not been adsorbed by the hydrotalcite layer have similar changes in the test results. At different preservation temperatures, the sulfur autotrophic denitrifying bacteria biofilm preserved at −20° C. has a higher content of living cells. At the three preservation temperature conditions, the contents of the early apoptotic cells, the late apoptotic cells and the dead cells are very close. At the same time, in the pilot operation system with good denitrification effect, the proportion of living cells of the sulfur autotrophic denitrifying bacteria biofilm is only 51.5%±4.9%, which is lower than that of the sulfur autotrophic denitrifying bacteria biofilm preserved at −20° C. The above results indicate that if higher concentration of sulfate presents in the sample, the test results of the cell activity state are significantly affected, resulting in failure to determine the optimum preservation temperature.

What is claimed is:

1. A method for determining an optimum preservation temperature of a sulfur autotrophic denitrifying bacteria biofilm, comprising: determining a cell activity state of the sulfur autotrophic denitrifying bacteria biofilm preserved at different temperatures by flow cytometry; and determining a preservation temperature of the cell activity state closest to the cell activity state of the sulfur autotrophic denitrifying bacteria in a pilot operation as the optimum preservation temperature, wherein the determining the cell activity state of the sulfur autotrophic denitrifying bacteria biofilm comprises determining contents of living cells, early apoptotic cells, late apoptotic cells and dead cells.

2. The method according to claim 1, wherein the determining the cell activity state of the sulfur autotrophic denitrifying bacteria biofilm by flow cytometry comprises the following steps:
   (1) preparing a test sample solution of the sulfur autotrophic denitrifying bacteria biofilm: diluting a sample of the sulfur autotrophic denitrifying bacteria biofilm with a first buffer; uniformly mixing and then passing through a hydrotalcite-containing filter device; centrifuging the filtered sample, and retaining a supernatant; then washing the cells with a pre-cooled second buffer; centrifuging and washing twice; and taking the supernatant as a sample and uniformly mixing with an appropriate amount of 10× Annexin V Binding Buffer; and
   (2) determining the cell activity state of each sample solution by flow cytometry.

3. The method according to claim 2, wherein a pH value of the first buffer is 6.2-6.8.

4. The method according to claim 2, wherein a dilution volume ratio of the first buffer to the sulfur autotrophic denitrifying bacteria biofilm is (8-10):1.

5. The method according to claim 2, wherein the filter device further comprises a nylon membrane with a pore size of 15-25 μm.

6. The method according to claim 2, wherein the first buffer comprises a phosphate buffer.

7. The method according to claim 3, wherein the first buffer comprises a phosphate buffer.

8. The method according to claim 5, wherein the first buffer comprises a phosphate buffer.

9. The method according to claim 2, wherein the first buffer comprises 39% v/v sodium dihydrogen phosphate and 61.0% v/v disodium hydrogen phosphate.

10. The method according to claim 3, wherein the first buffer comprises 39% v/v sodium dihydrogen phosphate and 61.0% v/v disodium hydrogen phosphate.

11. The method according to claim 5, wherein the first buffer comprises 39% v/v sodium dihydrogen phosphate and 61.0% v/v disodium hydrogen phosphate.

12. A method for rapidly starting a sulfur autotrophic denitrifying bacteria biofilm project, comprising: determining an optimum preservation temperature by the method of claim 2; placing a cultured mature sulfur autotrophic denitrifying bacteria biofilm in a preservation medium for preservation at the optimum preservation temperature; and after the activity is recovered, starting the sulfur autotrophic denitrifying bacteria biofilm project.

13. The method according to claim 12, wherein a COD concentration of the preservation medium is 40-50 mg/L, a concentration of $NH_4^+$—N is 0.3-0.5 mg/L, and a concentration of $NO_3^-$—N is 8-12 mg/L.

* * * * *